(12) United States Patent
Pursley

(10) Patent No.: US 8,703,229 B2
(45) Date of Patent: *Apr. 22, 2014

(54) METHOD OF MAKING CATHETERS WITH POROUS STRUCTURE FOR CARRYING AGENTS

(75) Inventor: Matt D. Pursley, Alpharetta, GA (US)

(73) Assignee: Volcano Corporation, San Diego, CA (US)

( * ) Notice: Subject to any disclaimer, the term of this patent is extended or adjusted under 35 U.S.C. 154(b) by 633 days.

This patent is subject to a terminal disclaimer.

(21) Appl. No.: 12/759,249

(22) Filed: Apr. 13, 2010

(65) Prior Publication Data

US 2010/0260923 A1    Oct. 14, 2010

Related U.S. Application Data

(63) Continuation-in-part of application No. 11/261,545, filed on Oct. 27, 2005, now Pat. No. 7,695,753, which is a continuation-in-part of application No. 11/234,514, filed on Sep. 22, 2005, now Pat. No. 7,776,380.

(60) Provisional application No. 60/612,673, filed on Sep. 22, 2004.

(51) Int. Cl.
*A61L 33/00* (2006.01)
*B05D 3/02* (2006.01)
*A61M 25/00* (2006.01)
*B05D 1/12* (2006.01)
*B05D 5/00* (2006.01)

(52) U.S. Cl.
USPC ........... 427/2.24; 427/2.1; 427/2.14; 427/2.3; 427/180; 427/421.1; 604/264; 604/265; 604/266; 604/508

(58) Field of Classification Search
USPC ........ 427/2.1, 2.24, 2.25, 2.26, 2.3, 457, 458, 427/487, 508, 541, 553, 558, 559, 565, 427/346; 604/264–266, 508
See application file for complete search history.

(56) References Cited

U.S. PATENT DOCUMENTS

| | | | | |
|---|---|---|---|---|
| 3,557,403 A * | 1/1971 | Lemelson et al. | ............... | 425/71 |
| 3,930,061 A * | 12/1975 | Scharfenberger | ............. | 427/483 |
| 5,395,332 A * | 3/1995 | Ressemann et al. | ........ | 604/103.1 |
| 5,529,820 A * | 6/1996 | Nomi et al. | ................... | 428/36.4 |
| 6,030,371 A * | 2/2000 | Pursley | .......................... | 604/527 |
| 6,945,970 B2 * | 9/2005 | Pepin | ............................ | 604/525 |
| 2003/0060871 A1 * | 3/2003 | Hill et al. | ..................... | 623/1.15 |

* cited by examiner

*Primary Examiner* — Cachet Sellman
(74) *Attorney, Agent, or Firm* — Jeffrey L. Thompson; Thompson & Thompson, P.A.

(57) ABSTRACT

A method of making catheters is disclosed in which the wall of the catheter has a porous structure for carrying additional agents, such as therapeutic agents, diagnostic agents and/or device enhancements. The method includes applying a base polymer material and an inert material over the outer surface of a core, and curing or consolidating the base polymer material to form a catheter having a porous polymer layer with the inert material contained within the pores thereof. The inert material can be applied with the base polymer material or in a separate step after the base polymer material has been partially cured or consolidated to form the porous polymer layer. Additional agents can be mixed with the inert material before it is applied to the catheter, or can be applied to the porous polymer layer of the catheter in a separate step after the inert material is removed therefrom.

32 Claims, 7 Drawing Sheets

METHOD OF MAKING CATHETERS WITH POROUS STRUCTURE FOR CARRYING AGENTS

RELATED APPLICATIONS

This application is a continuation-in-part of U.S. patent application Ser. No. 11/261,545 filed on Oct. 27, 2005, now U.S. Pat. No. 7,695,753, which was a continuation-in-part of U.S. patent application Ser. No. 11/234,514 filed on Sep. 22, 2005, now U.S. Pat. No. 7,776,380, which claims priority of U.S. Provisional Application No. 60/612,673 filed on Sep. 22, 2004. The content of these prior applications are incorporated herein by reference.

BACKGROUND OF THE INVENTION

1. Field of the Invention

The present invention relates generally to methods of manufacturing medical tubing. In particular, the present invention relates to methods of making catheters having a porous structure in which additives, such as therapeutic agents, diagnostic agents or device enhancements, can be carried.

2. Description of the Related Art

Medical tubing and catheters are widely employed for a variety of treatment and diagnostic procedures involving, for example, the administration of fluid medications and devices into a patient and the removal of fluids from the patient. In this application, the terms "catheter" and "medical tubing" will be used interchangeably to refer to the same structure.

The ultimate use for which medical tubing is designed requires that the tubing have certain physical characteristics. For example, a catheter must be sufficiently stiff or rigid to enable its insertion and movement through narrow body orifices and channels and, in some applications, must also be able to withstand a high bursting pressure. On the other hand, a catheter must be sufficiently soft and flexible so that it may readily conform to body shapes so as not to cause injury to the interior wall of a patient's vessel as it is advanced. In addition, a catheter must be of sufficient mechanical strength to resist tearing during normal use, such as when the catheter is removed against tissue resistance.

In many medical devices, the polymer used to construct these devices is first compounded with additives, such as coloring agents, plastisizers, and opacifiers to obtain optimum properties of the medical device for which the polymer is used. Such compounding generally involves adding the desired additive to pellets of the polymer and running the mix through a compounder (e.g., an extruder) where the polymer is sheared apart and inherently blends the polymer and additive together. After manufacturing, the devices are often coated with things to reduce friction, improve blood compatibility, or provide therapeutic benefits. Such surface coatings are difficult to accomplish because the surface must be prepared correctly and the coatings are often rubbed or worn off.

The Applicant previously developed a method for nonextrusion manufacturing of catheters, which is described in U.S. Pat. No. 6,030,371. In this existing method, a catheter is formed by spraying a fine polymer particulate, or solvenated polymer particulate, over a core to form a polymer shell of the catheter. The polymer material can be varied over the length of the catheter by using different hardness polymers to gradually vary the hardness of the catheter. The '371 patent teaches that the different hardness polymers can be colored to provide visual confirmation of the transition of hardness. The '371 patent also teaches the application of an opacifier material with the polymer material, or between layers of the polymer material. The polymer and opacifier materials are consolidated, for example, by heating in an oven.

Existing catheter manufacturing methods have not recognized the significant advantages that can be obtained by developing a catheter having a porous structure that can be used to carry therapeutic agents, diagnostic agents, device enhancements, and/or other desired agents into a patient's body.

SUMMARY OF THE INVENTION

The present invention provides a method of making catheters in which the side wall of the catheter has a porous structure for carrying agents, such as therapeutic agents, diagnostic agents and/or device enhancements. The method includes providing a core having an outer surface, applying a base polymer material and an inert material, such as silicone, over the outer surface of the core, and curing or consolidating the base polymer material to form a catheter having a porous polymer layer with the inert material contained within the pores of the porous polymer layer. The inert material, which can be a liquid or a solid, can be applied with the base polymer material, or the inert material can be applied in a separate step after the base polymer material has been partially cured or consolidated to form the porous polymer layer. Agents, such as therapeutic agents, diagnostic agents, and/or device enhancements, can be mixed with the inert material before the inert material is applied to the catheter, or such agents can be applied to the porous polymer layer of the catheter in a separate step after the inert material is removed from the pores thereof.

According to a broad aspect of the present invention, a method of making a catheter is provided, comprising: providing a core having an outer surface; applying a nonextruded layer of base polymer material over a length of the outer surface of the core; partially consolidating the base polymer material; filling voids left in the partially consolidated base polymer material with an inert material; completing the consolidation of the base polymer material with the inert material in the voids to thereby form a catheter having a porous polymer layer with inert material contained within the pores thereof; removing the inert material from the pores of the porous polymer layer; and filling the pores of the porous polymer layer with an agent after removing the inert material therefrom.

According to another broad aspect of the present invention, a method of making catheters is provided, comprising: providing a core having an outer surface; applying a nonextruded layer containing a base polymer material and an inert material over a length of the outer surface of the core; consolidating the base polymer material to thereby form a catheter having a porous polymer layer with inert material contained within the pores thereof; removing the inert material from the pores of the porous polymer layer; and filling the pores of the porous polymer layer with an agent after removing the inert material therefrom.

According to another broad aspect of the present invention, a method of making catheters is provided, comprising: providing a core having an outer surface; applying a base polymer material and an agent over a length of the outer surface of the core using electrostatic deposition; and curing the base polymer material to thereby form a catheter with the agent contained within a wall of the catheter.

Numerous other objects and features of the present invention will be apparent to those skilled in this art from the following description wherein there is shown and described exemplary embodiments of the present invention, simply by way of illustration of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

A method of making a catheter with a porous structure for carrying agents according to the present invention will now be described in detail with reference to FIGS. 1 to 13 of the drawings.

Figure 1:
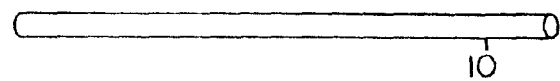
FIG. 1 shows a core mandrel over which a catheter will be constructed according to the present invention.

The method of making a catheter starts with a core mandrel 10, as shown in FIG. 1. The catheter will be constructed over the core mandrel 10 using much of the same technology disclosed in the Applicant's prior U.S. Pat. No. 6,030,371, which is incorporated herein by reference.

Figure 2:
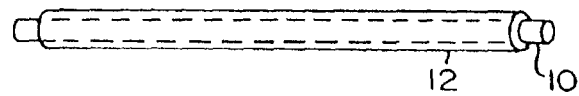
FIG. 2 shows a liner placed over the mandrel in the catheter manufacturing process of the present invention.

A catheter liner 12 is placed over the core mandrel 10, as shown in FIG. 2. The liner 12 can be formed of a variety of different materials, but is generally less than 20% of the intended wall thickness. As an example, a liner having a 0.00150 inch wall thickness of TFE can be used. Alternatively, the process of the present invention can be performed without a liner, whereby a polymer material is applied directly on the mandrel 10.

Figure 3:
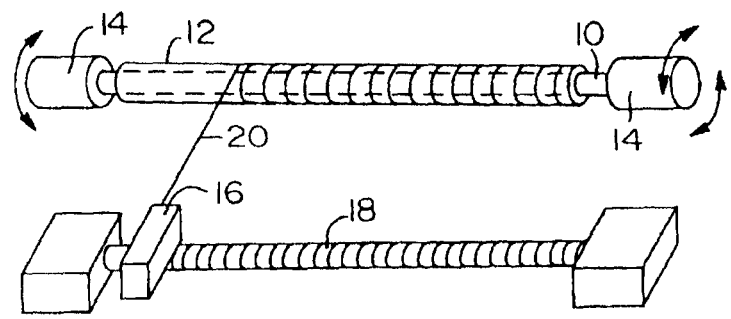
FIG. 3 shows a filament winding operation for applying a filament over the mandrel and liner in the catheter manufacturing process of the present invention.

A reinforcement filament is then applied over the liner 12, as shown in FIG. 3. During this operation, the mandrel/liner combination is loaded into rotating chucks 14. A filament winding head 16 travels on a screw carrier 18 longitudinally along the mandrel 10 to apply fibrous reinforcement filament 20 over the mandrel at a winding angle range of 0 to 90 degrees relative to the longitudinal axis of the catheter. For portions of the catheter that require great circumferential rigidity or kink resistance, a very tight winding angle (e.g., 80 to 90 degrees) of the reinforcement filament 20 can be used, and for portions of the catheter that require low rigidity, the reinforcement filament 20 can be applied in a low winding angle (e.g., 0 to 10 degrees). The winding angle of the reinforcement fiber 20 can be continuously varied over the length of the catheter by controlling the rotation speed of the mandrel 10 and the movement of the filament winding head 16 along the support 18.

Figure 4:
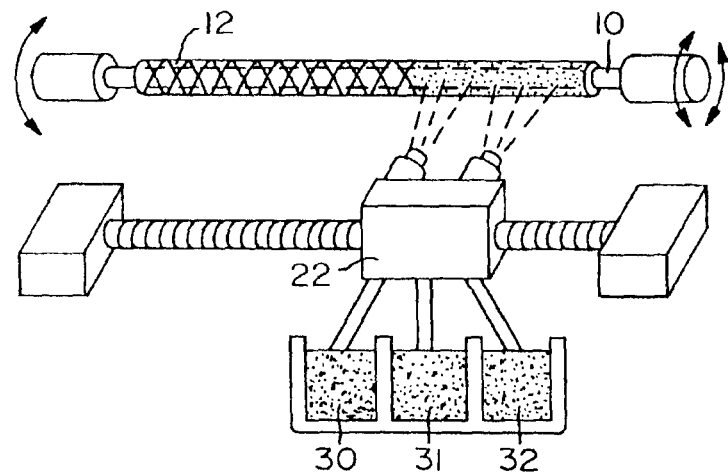
FIG. 4 shows a plurality of base polymer materials and an opacifier material being applied over the filament winding according to the catheter manufacturing process of the present invention.

At either the same time or after the reinforcement filament is applied, an atomizing spray head 22 traverses the mandrel/liner, as shown in FIG. 4. The spray head 22 applies an atomized spray that fuses to the substrate surface the sprays impinge upon (i.e., the mandrel 10, the liner 12, the reinforcement fiber 20, or the previous layer of polymer material). The substrate can be preheated to ensure complete fusion of the sprayed polymer to the substrate. This preheating can be accomplished with infrared, hot air, or resistance heating of the core mandrel 10 or other suitable means.

A suitable atomizing spray head 22 according to the present invention is described in detail in the Applicant's prior U.S. Pat. No. 6,030,371. The atomizing spray head 22 is connected to one or more containers 30 and 31 of polymer materials having varying degrees of hardness or other desired properties. The atomizing spray head 22 can also be connected to a container 32 of an opacifier material, such as tungsten.

While the mandrel/liner is spinning, the atomizing spray head 22 traverses along a path parallel to the axis of the rotating mandrel/liner. As it traverses this path, a metering valve (not shown) can be set such that only the harder polymer (e.g., from the container 30) is applied at what will be the proximal end of the catheter. As the head 22 traverses the mandrel/liner, the metering valve is controlled such that it ports to the harder polymer to a lesser degree and to the softer polymer (e.g., from the container 31) to a higher degree until finally only the softest polymer is applied at the distal tip of the catheter, which will serve as the soft distal tip of the catheter. The different hardness polymer materials used in the present invention can be colored to provide visual confirmation of the transition of hardness.

In a similar fashion, opacifying powder can be selectively applied from the container 32. In one example, a single layer of polymer material can be applied as the filaments are placed. The single layer of polymer material can be followed by a layer of opacifier material and another layer of polymer material. A significant benefit of applying opacifier in this manner is that the movement of the head 22 can be paused momentarily to apply circumferential rings of high opacifier concentration, which serve as markers when the catheter is used under X-ray.

The atomizing spray head 22 can also use electrostatic deposition to control application of the polymer materials to the mandrel/liner 10, 12. Electrostatic deposition uses the principal of "opposites attract" to cause the polymer materials to cling to the mandrel/liner 10, 12 during application. The polymer materials are fed from their supply reservoirs 30-32 to the spray head 22 where a low amperage, high voltage charge is imparted to the polymer materials. The mandrel/liner 10, 12 is electrically grounded. When sprayed from the spray head 22, the polymer materials are attracted to the grounded mandrel/liner's surface and held there by electrostatic force until the materials are cured or consolidated.

The present invention also includes process steps that create a porous structure in the catheter wall for carrying agents, such as therapeutic agents, diagnostic agents and/or device enhancements. These process steps will be described with reference to FIGS. 5 to 9 of the drawings.

Figure 5:
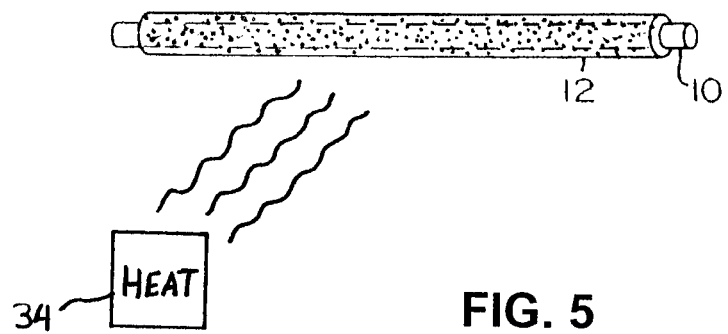
FIG. 5 shows a process step of heating the base polymer material to partially cure or consolidate the material.

In FIG. 5, the base polymer coated member 12 is heated by a heat source 34 to a sufficient temperature and for a sufficient time to partially consolidate the base polymer material. The heat is removed before the base polymer material is fully consolidated. When the heat is removed, the partially consolidated polymer material solidifies and creates a catheter body formed by sections that have melted and sections that have not melted. The partially consolidated polymer material has voids formed therein into which a liquid material can be wicked or otherwise infused.

Figure 6:
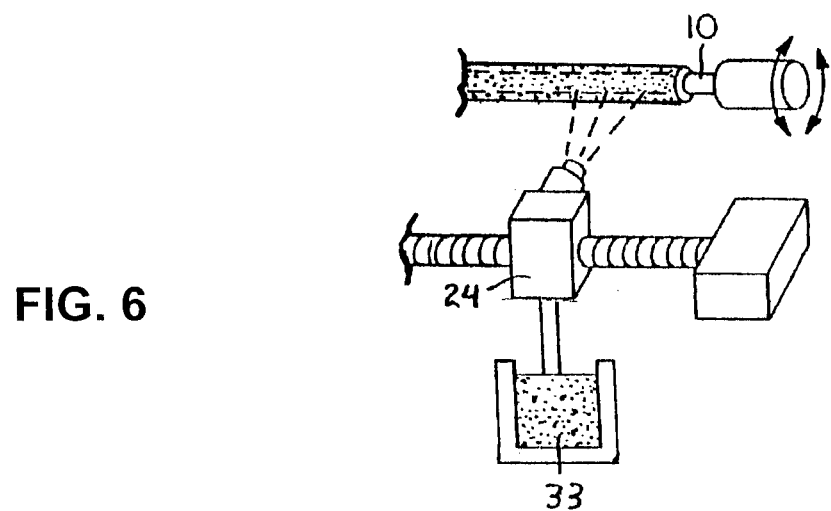
FIG. 6 shows a process step of applying an inert material over the partially cured or consolidated base polymer material.

In FIG. 6, an inert material 33, such as liquid silicone, is sprayed onto the outer surface of the partially consolidated base polymer material using a spray head 24. An inert material in liquid form can also be applied to the partially consolidated base polymer material by brushing or dipping or other known methods. The inert material wicks or otherwise infuses into the voids left by the partially consolidated base polymer material. The inert material can be either a liquid, such as liquid silicone, or a solid, such as a salt, and is selected from materials that will not bond with the base polymer material when the base polymer material is consolidated. This allows the inert material to be removed from the base polymer material later in the process, as explained below.

Figure 7:
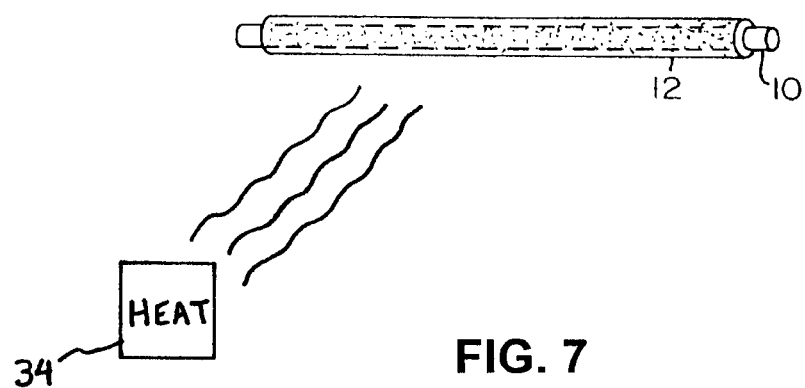
FIG. 7 shows a process step of heating the base polymer material to completely cure or consolidate the base polymer material, while the inert material remains contained therein.

In FIG. 7, the base polymer coated member 12 is again heated by a heat source 34 to a sufficient temperature and for a sufficient time to completely consolidate the base polymer material with the inert material in the voids thereof. A catheter structure is thereby formed having a porous polymer layer with an inert material contained within the pores thereof.

Figure 8:
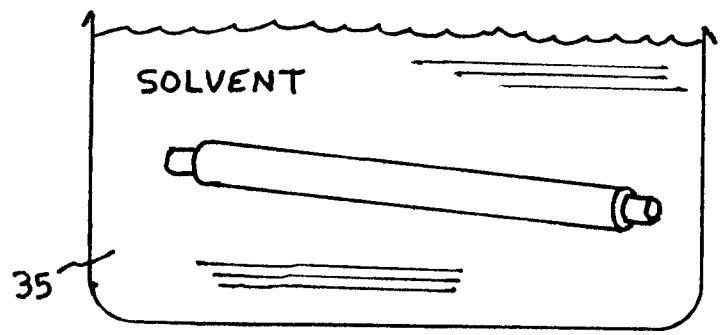
FIG. 8 shows a process step of washing the inert material from the base polymer material using a solvent to create a porous polymer layer.

In FIG. 8, a solvent 35 is used to wash out the inert material from the pores of the catheter structure. Once the inert material is washed out, the catheter structure has a porous polymer layer with true voids formed in the polymer layer. The voids in the polymer layer can be filled with an agent, as explained below.

Figure 9:
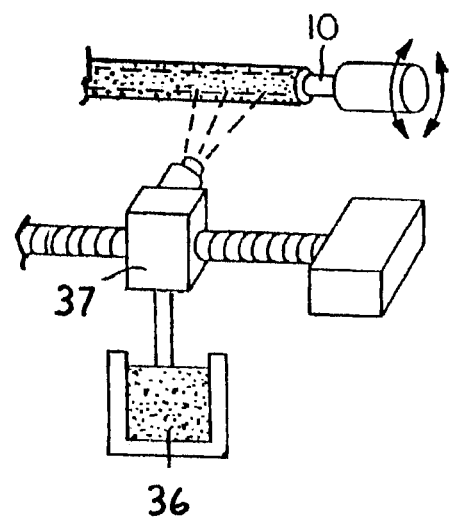
FIG. 9 shows a process step of applying an agent, such as a therapeutic agent, diagnostic agent or device enhancement, to the porous polymer layer.
Figure 10:
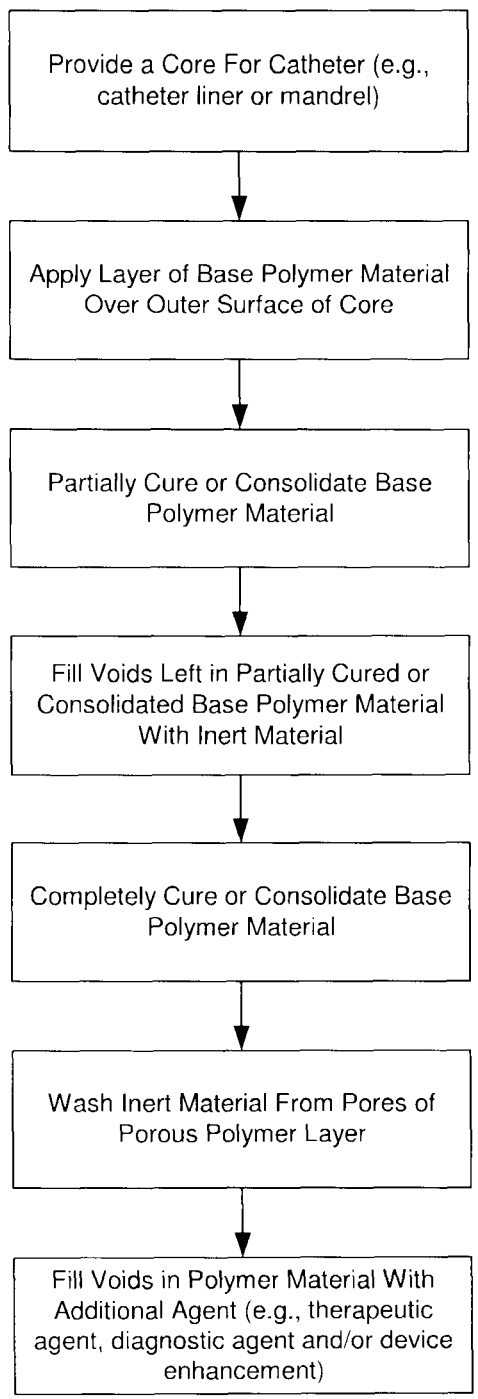
FIG. 10 is a process flow chart showing a series of process steps for making a catheter according to one embodiment of the present invention.
Figure 11:
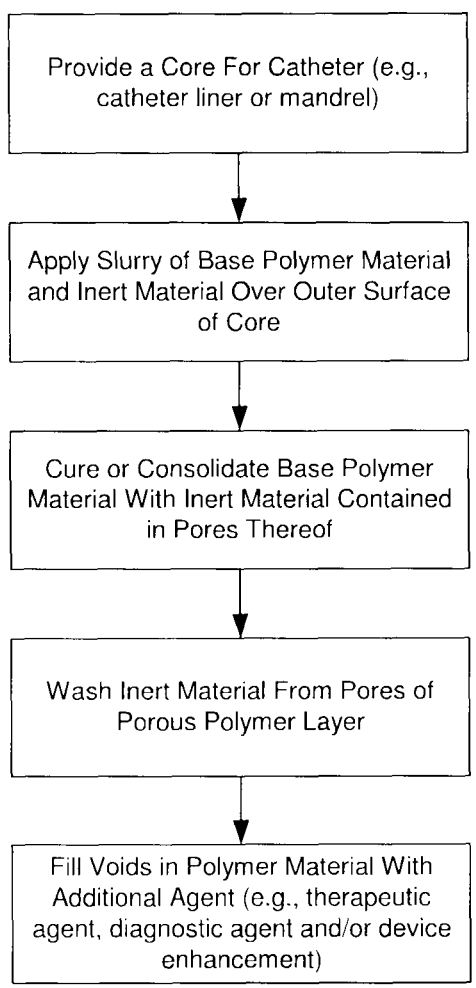
FIG. 11 is a process flow chart showing a series of process steps for making a catheter according to another embodiment of the present invention.
Figure 12:
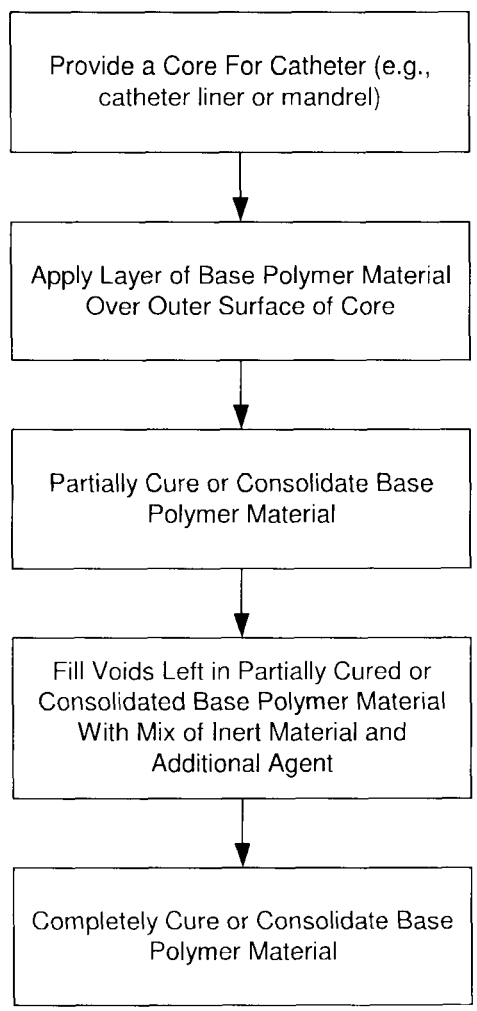
FIG. 12 is a process flow chart showing a series of process steps for making a catheter according to another embodiment of the present invention.
Figure 13:
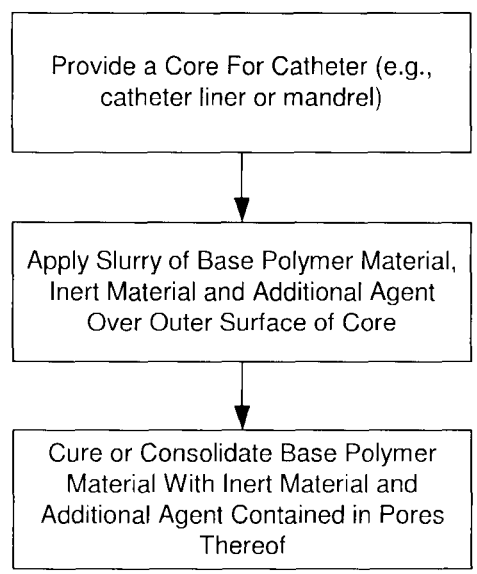
FIG. 13 is a process flow chart showing a series of process steps for making a catheter according to another embodiment of the present invention.

In FIG. 9, an agent 36, such as a therapeutic agent, diagnostic agent and/or device enhancement, is applied to the porous polymer layer. The agent 36 can be applied by spraying with a spray head 37, as shown in FIG. 9, or it can be applied by dipping, brushing, or other methods that allow the agent to be wicked or otherwise infused into the porous polymer.

The process described above and shown in FIGS. 5 to 9 provides a catheter having an agent, such as a therapeutic agent, diagnostic agent and/or device enhancement, carried in a porous structure on the outer surface of the catheter. The process of creating the porous structure using an inert material allows the agent to be added after the high temperature consolidation process for the polymer has been completed. Thus, agents that cannot withstand high temperatures can be effectively added to and carried by the catheter using the process of the present invention. A flow chart of the process steps according to this embodiment of the present invention is provided in FIG. 10.

In another embodiment, an inert material can be mixed with the polymer material and applied with the polymer material in the process step shown in FIG. 4. The polymer material can then be completely consolidated by heating, as shown by the process step in FIG. 7 (in this case, the partial consolidation step shown in FIG. 5 and the separate step of applying inert material shown in FIG. 6 can both be eliminated). The catheter formed by the consolidated base polymer material with inert material contained therein can then be washed in solvent to remove the inert material, as shown by the process step of FIG. 8, thereby forming a catheter structure having a porous polymer layer. An agent can then be applied to the porous polymer layer, as shown by the process step of FIG. 9. A flow chart of the process steps according to this embodiment of the present invention is provided in FIG. 11.

For agents that can withstand high temperatures, or if a method of curing or consolidating the polymer materials is used that does not require high temperatures, an inert material, such as silicone, can be used as a carrier for the agent (the agent is mixed in). In this case, the same process as described above can be used, except that the inert material would not have to be washed out. For example, the inert material with an agent mixed in could be applied in the process step shown in FIG. 6, and the catheter would be finished upon completing the consolidation step shown in FIG. 7 (or upon curing or consolidating the polymer materials using non-heating techniques as described herein). A flow chart of the process steps according to this embodiment of the present invention is provided in FIG. 12.

In another embodiment, the inert material and agent can both be mixed in with the base polymer material and applied to the outer surface of the core together in the process step shown in FIG. 4. In this case, the process steps shown in FIGS. 5, 6, 8 and 9 could be eliminated, and the catheter would be finished upon completing the consolidation step shown in FIG. 7 (or upon curing or consolidating the polymer materials using non-heating techniques as described herein). A flow chart of the process steps according to this embodiment of the present invention is provided in FIG. 13. The additive material can include polymer materials used to modify the base polymer material. For example, the additive material can be silicones, PTFE, paraffins, plastisizers and lubricants. The additive material can also include nonpolymeric materials, such as therapeutic agents and diagnostic agents. For example, the additive material can be therapeutic agents such as anticoagulants, anti-inflammatories, oxides, and gene therapy materials. The additive material can also be diagnostic agents other than opacifiers, or coloring agents separate from the base polymer materials.

After the base polymer material is completely cured or consolidated, the catheter can be rough-sized by passing a cutter over the surface of the catheter and then polished. The catheter body can then be removed from the rotating chucks 14 and is ready for finishing operations, such as curving or hubbing.

In the embodiments described above, curing or consolidation is accomplished by heating. However, in some cases consolidation can be better accomplished by other known techniques, such as driving off solvent from a solution. Other techniques can also be used for curing or consolidating the polymer materials to accomplish the desired results. For example, the polymer materials can be applied either as a solvenated mixture or a dry system, and then cured by adding or removing energy using the following techniques:

a) Exposing the applied polymer to a light source, such as UV light, to activate or excite the polymers (applied energy);

b) Applying acoustic energy with an external source, similar to ultrasonic welding;

c) Applying energy through a vibration source that vibrates the mandrel; and/or d) Remove energy through cooling (convective, conductive or radiant). For example, a condensation cure system can be used in which removal of a condensate such as water is necessary.

The above techniques for curing the polymer materials are most applicable for thermosetting systems, but also can be applied to thermoplastics. In some cases, heat can be used to cure or consolidate the polymer materials, while at the same time energy can be transferred into or out of the system to keep the system cool to avoid overheating the agents.

In addition to the curing and consolidating techniques described above, the invention can also use polymers that comprise multipart systems. For example, epoxies, urethanes, and silicones are frequently supplied in two parts. When the two parts are mixed together, the constituents come into contact, react chemically, and cross link. Polymer materials provided as multipart epoxy systems can be applied electrostatically, and then allowed to react and cure after they are mixed during the application process. For example, one part of the epoxy system could be applied to the mandrel/liner 10, 12 first, and the second part of the epoxy system could then be applied over the first part, or both parts of the epoxy system could be applied at the same time. Multipart systems for urethanes and silicones can also be applied in this manner.

The curing process for multipart polymer systems, such as those used for epoxies, urethanes and silicones, can be controlled by adding or subtracting energy to enhance or promote the process. For example, a two part system might react slowly at low temperatures, but can be sped up by applying energy. Depending on whether the chemical reaction is exothermic or endothermic, energy can be added or removed to enhance the reaction or to control the temperature of the reaction.

The agent(s) used in the present invention can be therapeutic agents such as anticoagulants, anti-inflammatories, oxides, and gene therapy materials, and/or diagnostic agents. The agent(s) can also device enhancements, such as opacifiers.

The present invention provides techniques for creating catheters having agents carried in a porous structure on the catheter. The process of creating the porous structure and applying the agents to the catheter is accomplished in ways that avoid having the agents subject to high temperatures. That is catheter can be maintained at a relatively "cool" temperature after the agents have been applied. This allows a wide variety of agents to be applied to the catheter, including agents that are unable to withstand high temperatures without being degraded or destroyed.

The terms "cure" and "consolidate" have been used interchangeably in this application to refer to the toughening or hardening of polymer materials used to make catheters according to embodiments of the present invention. It will be understood by those in the art that such toughening or hardening of the polymer materials can be brought about by chemical additives, ultraviolet radiation, acoustic energy, electron beam, heat, or other known techniques. As used in the claims, the terms "consolidate," "consolidating" and "consolidation" are intended to cover all such techniques for curing or consolidating polymer materials.

While the invention has been specifically described in connection with specific embodiments thereof, it is to be understood that this is by way of illustration and not of limitation, and the scope of the appended claims should be construed as broadly as the prior art will permit.

What is claimed is:

1. A method of making catheters, comprising:
providing a core having an outer surface;
applying a nonextruded layer of base polymer material over a length of said outer surface of the core;
partially consolidating the base polymer material;
filling voids left in the partially consolidated base polymer material with an inert material;
completing the consolidation of the base polymer material with the inert material in the voids to thereby form a catheter having a porous polymer layer with inert material contained within the pores thereof;
removing the inert material from the pores of the porous polymer layer; and
filling the pores of the porous polymer layer with an agent after removing the inert material therefrom.

2. The method according to claim 1, wherein said agent is selected from the group consisting of therapeutic agents, diagnostic agents, and device enhancements.

3. The method according to claim 1, wherein said agent is an opacifier.

4. The method according to claim 1, wherein said base polymer material is applied over said core by electrostatic deposition.

5. The method according to claim 1, wherein at least one of said steps of partially consolidating the base polymer material and completing the consolidation of the base polymer material comprises exposing the polymer material to an applied energy source to cure said polymer material.

6. The method according to claim 5, wherein said applied energy source comprises an ultraviolet light source.

7. The method according to claim 1, wherein at least one of said steps of partially consolidating the base polymer material and completing the consolidation of the base polymer material comprises applying acoustic energy to cure said polymer material.

8. The method according to claim 1, wherein at least one of said steps of partially consolidating the base polymer material and completing the consolidation of the base polymer material comprises applying vibration energy through said core to cure said polymer material.

9. The method according to claim 1, wherein at least one of said steps of partially consolidating the base polymer material and completing the consolidation of the base polymer material comprises removing a condensate to cure said polymer material.

10. The method according to claim 1, wherein at least one of said steps of partially consolidating the base polymer material and completing the consolidation of the base polymer material comprises causing two parts of said base polymer material to come into contact with each other, react chemically and cross link.

11. The method according to claim 10, wherein said at least one step of partially consolidating the base polymer material and completing the consolidation of the base polymer material further comprises adding or subtracting energy to said two parts of said base polymer material to promote curing.

12. The method according to claim 10, wherein said base polymer material is selected from the group consisting of epoxies, urethanes, and silicones.

13. A method of making catheters, comprising:
providing a core having an outer surface;
applying a nonextruded layer containing a base polymer material and an inert material over a length of said outer surface of the core;

consolidating the base polymer material to thereby form a catheter having a porous polymer layer with inert material contained within the pores thereof;

removing the inert material from the pores of the porous polymer layer; and filling the pores of the porous polymer layer with an agent after removing the inert material therefrom.

14. The method according to claim 13, wherein said agent is selected from the group consisting of therapeutic agents, diagnostic agents, and device enhancements.

15. The method according to claim 13, wherein said agent is an opacifier.

16. The method according to claim 13, wherein said base polymer material and said inert material are applied over said core by electrostatic deposition.

17. The method according to claim 13, wherein said step of consolidating the base polymer material comprises exposing the polymer material to an applied energy source to cure said polymer material.

18. The method according to claim 17, wherein said applied energy source comprises an ultraviolet light source.

19. The method according to claim 13, wherein said step of consolidating the base polymer material comprises applying acoustic energy to cure said polymer material.

20. The method according to claim 13, wherein said step of consolidating the base polymer material comprises applying vibration energy through said core to cure said polymer material.

21. The method according to claim 13, wherein said step of consolidating the base polymer material comprises removing a condensate to cure said polymer material.

22. The method according to claim 13, wherein said step of consolidating the base polymer material comprises causing two parts of said base polymer material to come into contact with each other, react chemically and cross link.

23. The method according to claim 22, wherein said step of consolidating the base polymer material further comprises adding or subtracting energy to said two parts of said base polymer material to promote curing.

24. The method according to claim 22, wherein said base polymer material is selected from the group consisting of epoxies, urethanes, and silicones.

25. A method of making catheters, comprising:

providing a core having an outer surface;

applying a base polymer material and an agent other than an opacifier over a length of said outer surface of the core using electrostatic deposition; and curing the base polymer material to thereby form a catheter with the agent contained within a wall of the catheter;

said agent being selected from the group consisting of silicones, PTFE, paraffins, plastisizers, lubricants, nonpolymeric therapeutic agents, and nonpolymeric diagnostic agents.

26. The method according to claim 25, wherein said agent is selected from the group consisting of nonpolymeric therapeutic agents and nonpolymeric diagnostic agents.

27. The method according to claim 25, wherein said step of curing the base polymer material comprises exposing the polymer material to an applied energy source.

28. The method according to claim 27, wherein said applied energy source comprises an ultraviolet light source.

29. The method according to claim 25, wherein said step of curing the base polymer material comprises applying acoustic energy to said polymer material.

30. The method according to claim 25, wherein said step of curing the base polymer material comprises applying vibration energy through said core to said polymer material.

31. The method according to claim 25, wherein said step of curing the base polymer material comprises causing two parts of said base polymer material to come into contact with each other, react chemically and cross link.

32. The method according to claim 31, wherein said base polymer material is selected from the group consisting of epoxies, urethanes, and silicones.

* * * * *